(12) United States Patent
Pisacane

(10) Patent No.: US 11,672,627 B2
(45) Date of Patent: *Jun. 13, 2023

(54) CLEANING DEVICE WITH KITE TAIL SWAB

(71) Applicant: Foamtec International Co., Ltd., Waco, TX (US)

(72) Inventor: Ferdinand Frederick Pisacane, San Diego, CA (US)

(73) Assignee: Foamtec International Co., Ltd., Waco, TX (US)

( * ) Notice: Subject to any disclaimer, the term of this patent is extended or adjusted under 35 U.S.C. 154(b) by 377 days.

This patent is subject to a terminal disclaimer.

(21) Appl. No.: 16/858,982

(22) Filed: Apr. 27, 2020

(65) Prior Publication Data

US 2020/0254491 A1 Aug. 13, 2020

Related U.S. Application Data

(63) Continuation of application No. 15/094,781, filed on Apr. 8, 2016, now Pat. No. 10,828,128, which is a continuation of application No. 14/196,433, filed on Mar. 4, 2014, now Pat. No. 9,339,349.

(60) Provisional application No. 61/773,284, filed on Mar. 6, 2013.

(51) Int. Cl.
| | |
|---|---|
| *A61B 90/70* | (2016.01) |
| *B08B 9/00* | (2006.01) |
| *B08B 9/02* | (2006.01) |
| *B08B 9/027* | (2006.01) |
| *B08B 9/04* | (2006.01) |
| *B08B 1/00* | (2006.01) |

(52) U.S. Cl.
CPC .............. *A61B 90/70* (2016.02); *B08B 1/006* (2013.01); *B08B 9/00* (2013.01); *B08B 9/02* (2013.01); *B08B 9/027* (2013.01); *B08B 9/04* (2013.01); *A61B 2090/701* (2016.02)

(58) Field of Classification Search
CPC ... A61B 2090/701; A61B 90/70; A61B 1/122; F41A 29/02; B08B 9/00; B08B 9/0436; B08B 1/006; B08B 9/04; B08B 9/02; B08B 9/027; B08B 1/003
USPC ........................................................ 15/209.1
See application file for complete search history.

(56) References Cited

U.S. PATENT DOCUMENTS 852,748 A 5/1907 True
1,164,665 A * 12/1915 Reeves ................... F41A 29/02
42/95

(Continued)

FOREIGN PATENT DOCUMENTS

BE 528464 A 3/1957
DE 2614031 A1 10/1977

(Continued)

OTHER PUBLICATIONS

International Search Report and Written Opinion from related PCT Application No. PCT/US14/21365 dated Jul. 1, 2014.

*Primary Examiner* — David G Cormier
*Assistant Examiner* — Thomas Bucci
(74) *Attorney, Agent, or Firm* — Zeman-Mullen & Ford, LLP

(57) ABSTRACT

A cleaning device, especially an instrument cleaning device, having a thin, flexible threadlike object with a first straight end and a second looped end and a swab member attached to the looped end.

17 Claims, 2 Drawing Sheets

(56) References Cited

U.S. PATENT DOCUMENTS

| | | | | | |
|---|---|---|---|---|---|
| 2,303,660 | A | * | 12/1942 | Elgeva | A46B 5/00 15/244.1 |
| 2,537,149 | A | * | 1/1951 | McKean | A47L 17/00 15/104.18 |
| 2,642,602 | A | * | 6/1953 | Kelly | B08B 9/0436 15/104.19 |
| 3,205,518 | A | * | 9/1965 | Romaine | B08B 9/0436 42/95 |
| 3,708,820 | A | * | 1/1973 | Schultea | F41A 29/02 42/95 |
| 4,215,478 | A | * | 8/1980 | Thomas | A61C 15/045 433/25 |
| 4,497,082 | A | * | 2/1985 | Kogasaka | F41A 29/02 42/95 |
| 5,168,593 | A | * | 12/1992 | Poje | A61B 90/70 401/289 |
| 5,171,925 | A | * | 12/1992 | Mekler | F41A 29/02 42/95 |
| 5,183,461 | A | | 2/1993 | Hobbs | |
| 5,297,310 | A | * | 3/1994 | Cox | B08B 9/0436 15/106 |
| 5,657,570 | A | * | 8/1997 | Sigier Emmanuel | F41A 29/02 42/95 |
| 5,871,589 | A | * | 2/1999 | Hedge | F41A 29/02 42/95 |
| 7,367,151 | B1 | | 5/2008 | Black et al. | |
| 8,176,592 | B1 | * | 5/2012 | Carpenter | B08B 9/043 42/95 |
| 8,572,883 | B2 | | 11/2013 | Markle | |
| 9,339,349 | B2 | * | 5/2016 | Pisacane | B08B 9/04 |
| 10,828,128 | B2 | * | 11/2020 | Pisacane | A61B 1/122 |
| 2001/0016962 | A1 | * | 8/2001 | Moore | B08B 9/045 15/104.16 |
| 2004/0187893 | A1 | * | 9/2004 | Maguire, Jr. | A46B 3/18 134/8 |
| 2006/0102200 | A1 | * | 5/2006 | Esquenet | B08B 9/04 427/430.1 |
| 2011/0289705 | A1 | * | 12/2011 | Asano | A61B 1/122 15/104.05 |
| 2012/0145181 | A1 | * | 6/2012 | Slack | A61C 15/046 29/505 |
| 2012/0283616 | A1 | * | 11/2012 | Edme | A61F 13/38 604/1 |
| 2014/0082989 | A1 | * | 3/2014 | Canham | F41A 29/02 15/247 |
| 2014/0237748 | A1 | * | 8/2014 | Sweeney | B08B 1/006 15/210.1 |
| 2014/0250614 | A1 | | 9/2014 | Pisacane | |
| 2014/0276514 | A1 | | 9/2014 | Simon | |

FOREIGN PATENT DOCUMENTS

| | | |
|---|---|---|
| EP | 2769697 A1 | 8/2014 |
| GB | 24630 | 12/1912 |
| GB | 487754 A | 6/1938 |

* cited by examiner

CLEANING DEVICE WITH KITE TAIL SWAB

CROSS-REFERENCE TO RELATED APPLICATIONS

This application is a continuation of and claims the benefit of, and priority to U.S. Nonprovisional patent application Ser. No. 15/094,781, filed Apr. 8, 2016, currently pending, which is a continuation of U.S. Nonprovisional patent application Ser. No. 14/196,433 filed Mar. 4, 2014, now U.S. Pat. No. 9,339,349, which claims the benefit of, and priority to, provisional patent application having Ser. No. 61/773,284, filed Mar. 6, 2013, which applications are hereby incorporated by reference in their entireties.

FIELD OF INVENTION

The present invention generally relates to a cleaning device, especially an instrument cleaning device, having a kite tail like swab. More particularly, the present invention relates to a cleaning device which includes a rod member or filament like member having at least one end that terminates in a loop and a swab member attached to the loop.

BACKGROUND OF THE INVENTION

Medical devices and medical instruments are becoming more sophisticated and much smaller thereby enabling surgeons to reach rewrote parts of the body without the need for open surgery which exposes a much larger part of the body to the risk of outside infections. In addition, using these instruments results in lowering the complications of surgery and speeding up the recovery time for patients. However, these devices and instruments must be cleaned and decontaminated after use so that they can be reused in future procedures. This cleaning and decontamination process is often called reprocessing.

Reprocessing medical instruments and devices can become difficult with the newest and latest devices which often include miniscule channels and crevices that can be impossible to see and troublesome to access. In addition, the instruments and devices sometimes fail to come with adequate cleaning instructions or include cleaning instructions that are confusing and onerous to follow. As a result, many of these instruments and devices are reused without proper cleaning which can lead to severe risks for patients.

A University of Michigan study analyzed the cleanliness of 350 suction tips used to vacuum up fluids during surgery and found that 95 percent of them still contained debris after routine reprocessing. In another study, the Centers for Disease Control (CDC) conducted an investigation into seven individuals who contracted surgical-site bacterial infections after having knee or shoulder arthroscopy in a Houston hospital. The CDC found that the arthroscopic shavers that were used for the procedures contained residual bits of body tissue. Endoscopes and cannulas are even more worrisome to infectious disease experts in that millions of surgical procedures are performed each year using these instruments.

Surgical instruments like endoscopes and cannulas are typically cleaned with twisted metal wire brushes and pipe cleaning type devices. However, these types of cleaning devices can cause major problems including incomplete cleaning, damage to medical devices and instruments resulting from scratching, and metal fibers and other types of cleaning fibers left inside the instruments after cleaning. In addition, these types of cleaning devices are high in cost to produce and therefore need to be reused, thereby carrying the attendant risks of cross contamination.

Accordingly, there is a need for a simple, low cost cleaning device which overcomes these obstacles. There is also a particular need for a simple, low cost device specifically designed for cleaning medical instruments and medical devices such as endoscopes and cannulas without the risk of damaging the instruments and further risking infection to patients.

SUMMARY OF THE INVENTION

The present invention is directed to a cleaning device that includes a rod or filament like member having at least one end that terminates in a loop and a swab member attached to the loop. In one exemplary embodiment the rod member may comprise a polymer and, in particular, it may comprise an organic polymer thermoplastic such as, for example, polyether ether ketone so that the rod member results in a thin, flexible, threadlike object. In addition, the swab member may comprise a foam material and/or a microfiber material.

In another exemplary embodiment the rod member may have a first end that comprises a straight end and a second end that comprises a looped end. In yet another exemplary embodiment, the looped end may have a smaller diameter than the straight end. In still another embodiment, the looped end of the rod member may be longer in length than the straight end of the rod member and the swab member may be shorter in length than the looped end. In yet another exemplary embodiment of the cleaning device, the looped end of the rod member may be equal to or greater in length than the straight end of the rod member and the swab member may be longer in length than the looped end of the rod member.

With respect to the swab member of the cleaning device, the swab member may comprise a first end attached to the loop or looped end of the rod member and a second end comprising a tail. The tail may comprise two or more separate members. In addition, in one exemplary embodiment, the swab member may comprise one or more materials that are braided in relation to one another. In another exemplary embodiment, the swab member may comprise one or more materials that are twisted in relation to one another. For example, the swab member may comprise a foam material and a microfiber material that are braided or twisted in relation to one another.

In the exemplary embodiment of the cleaning device which includes a rod member having a first straight end and a second looped end and a swab member attached to the second looped end of the rod member, the outer circumference of the straight end may be larger than the outer circumference of the second looped end. In addition, the first straight end of the rod member may comprise two thicknesses of the second looped end of the rod member where the two thicknesses that comprise the straight end are fused or bonded together or co-extruded such that the straight and looped ends of the rod member are continuous with one another. Also, in a further aspect of the invention, the swab member may be attached to the second looped end of the rod member by having a portion of the second looped end of the rod member traversing through an end of the swab member such that the swab member is capable of being rotated about and through the second looped end of the rod member. This attachment would also enable the swab member to slide along the length of the second looped end of the rod member.

BRIEF DESCRIPTION OF THE DRAWINGS

The subject invention will hereinafter be described in conjunction with the appended drawing figures, wherein like numerals demote like elements.

DETAILED DESCRIPTION OF EXEMPLARY EMBODIMENTS

The cleaning device of the present invention generally provides a rod or filament like member having at least one end that terminates in a loop and a swab member attached to the loop. The swab member may have first and second ends where the first end is attached to the loop and the second end comprises a tail such as the tail of a kite where the tail can be of any length. The swab member may comprise one or more materials that can be braided or twisted with the tail end of the swab member comprising the unbraided or untwisted ends of the material or materials that comprise the swab member. In addition, the swab member may comprise a foam material and/or a microfiber material.

The rod member of the cleaning device may be comprised of a polymer having first and second ends where the first end is a straight end and the second end is a looped end. In addition, the rod member may comprise one continuous polymer rod with the looped end of the rod member comprising one thickness or diameter and the straight end of the rod member comprising two thicknesses or two diameters of the looped end of the rod. The two thicknesses or diameters of the polymer rod that form the straight end of the rod member may be fused or bonded together, laminated together, or co-extruded.

Figure 1:
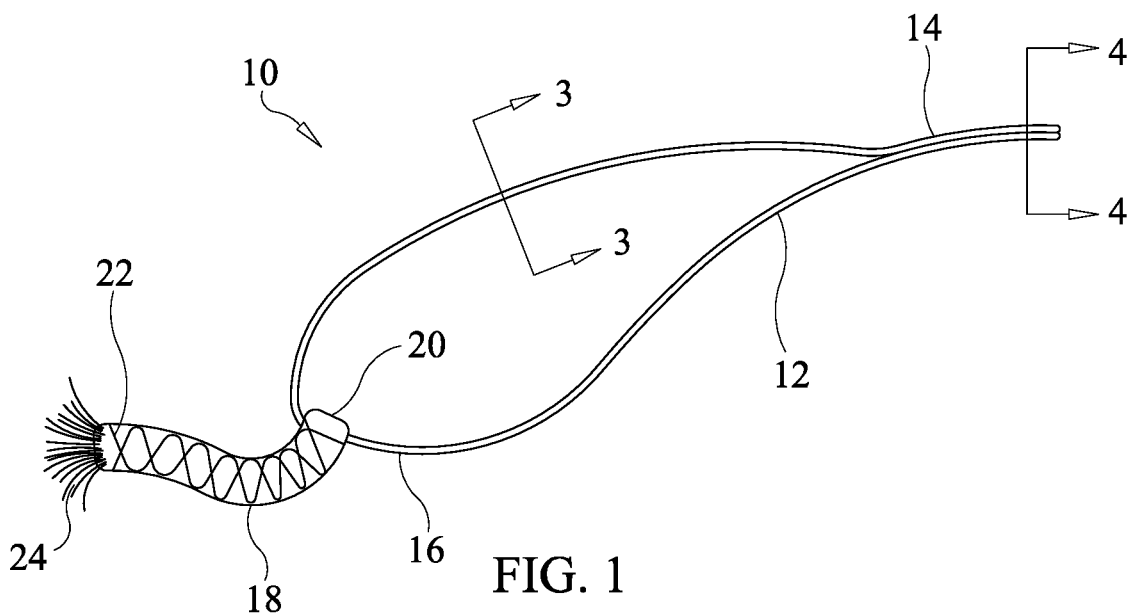
FIG. 1 is top plan view of one exemplary embodiment of the cleaning device of the present invention.

FIG. 1 shows a top plan view of one exemplary embodiment of the cleaning device of the present invention. Cleaning device 10 includes a rod member 12 having a first end 14 and a second end 16 where second end 16 comprises a looped end. Cleaning device 10 also includes a swab member 18 having a first end 20 and a second end 22 where first end 20 is attached to the second looped end 16 of rod member 12 and second end 22 comprises a tail 24 which can be like the tail of a kite where the tail can be of any length. Swab member 18 may comprise one or more materials that may comprise one or more fibers that can be braided or twisted with the tail end 24 of the swab member 18 comprising the unbraided and/or untwisted ends of the material (s) and/or fiber(s) that comprise the swab member 18. In addition, the swab member 18 may comprise a foam material and/or a microfiber material.

Figure 2:
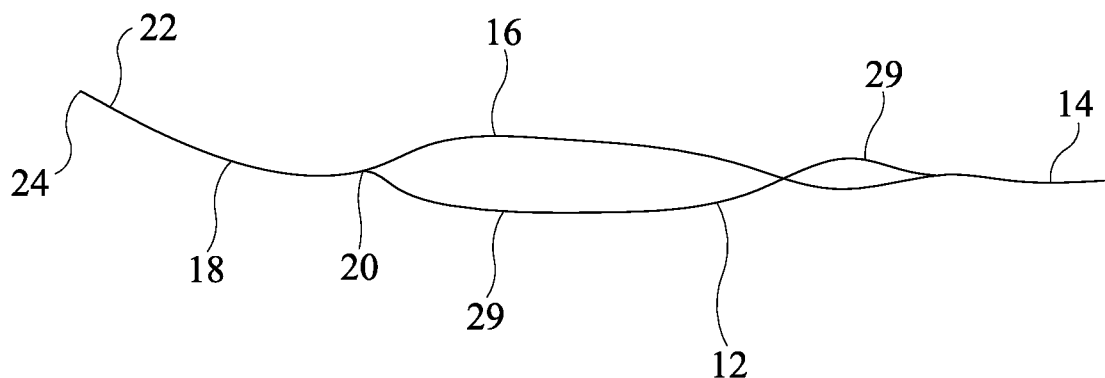
FIG. 2 is a side elevational view of the exemplary embodiment of the cleaning device of the present invention shown in FIG. 1.

A side elevational view of the exemplary embodiment of the cleaning device 10 shown in FIG. 1 is shown in FIG. 2. Rod member 12 of cleaning device 10 may be comprised of a polymer that may be flexible which is shown by the curved areas 29 of the second looped end 16 of rod member 12. Second looped end 16 of rod member 12 is larger than first end 14 of rod member 12 in the embodiment shown in FIGS. 1 and 2. The polymer comprising rod member 12 may be an organic polymer thermoplastic which, in one exemplary embodiment, may be a polyether ether ketone. The rod member is preferably a thin, flexible, threadlike object.

Figure 3:
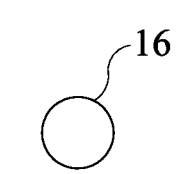
FIG. 3 is a magnified cross-sectional view of the exemplary embodiment of the cleaning device shown in FIG. 1 taken along line 3-3.
Figure 4:
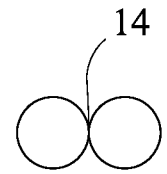
FIG. 4 is a magnified cross-sectional view of the exemplary embodiment of the cleaning device shown in FIG. 1 taken along line 4-4.

FIG. 3 is a magnified cross-sectional view of the exemplary embodiment of the cleaning device shown in FIG. 1 taken along line 3-3 and FIG. 4 is a magnified cross-sectional view of the exemplary embodiment of the cleaning device shown in FIG. 1 taken along line 4-4. As shown in FIGS. 3 and 4, the diameter of looped end 16 of rod member 12 is smaller than the diameter of straight end 14 of rod member 12. Likewise, the outer circumference of looped end 16 of rod member 12 is smaller than outer circumference of straight end 14 of rod member 12. Further as shown in FIGS. 3 and 4, straight end 14 of rod member 12 may comprise two thicknesses of second looped end 16 of rod member 12 where the two thicknesses that comprise the straight end 14 are fused or bonded together or co-extruded such that the straight and looped ends 14, 16 of rod member 12 are continuous with one another. In the exemplary embodiment shown in FIGS. 1 and 2, the looped end 16 of rod member 12 is greater or longer in length than straight end 14 of rod member 12. However, depending on the type of instrument that cleaning device 10 of the present invention is designed to clean, looped end 16 of rod member 12 may be equal in length to, or shorter in length than, straight end 14 of rod member 12.

In a further aspect of the invention, swab member 18 may be attached to second looped end 16 of rod member 12 by having a portion of second looped end 16 of rod member 12 traverse through a portion of first end 20 of swab member 18 such that swab member 18 is capable of being rotated about and through second looped end 16 of rod member 12. In addition, such attachment would allow swab member 18 to slide along the length of second looped end 16 of rod member 12. Further, in one exemplary embodiment, swab member 18 may be shorter in length than second looped end 16 of rod member 12 and in another exemplary embodiment swab member 18 may be longer in length than second looped end 16 of rod member 12. In still a further embodiment, swab member 18 may be equal in length to second looped end 16 of rod member 12.

Figure 5:
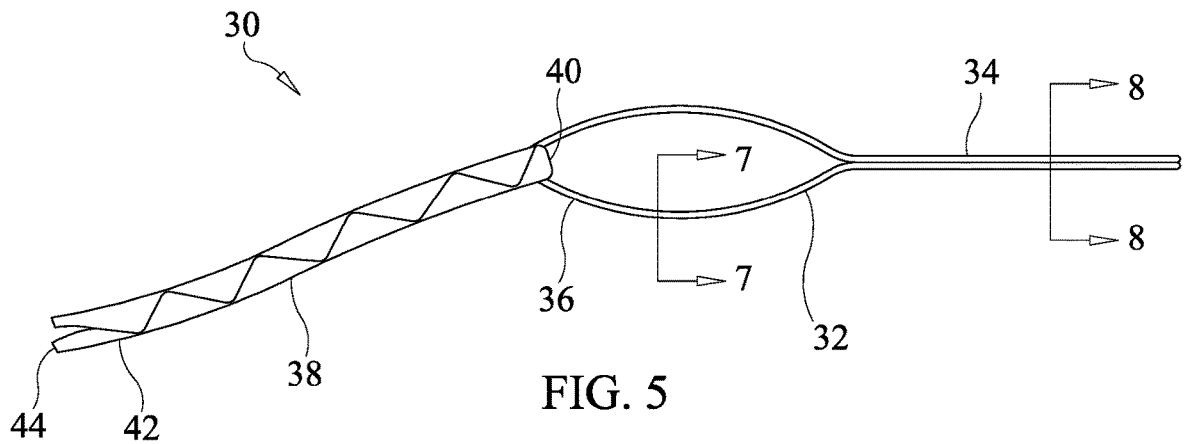
FIG. 5 is a top plan view of another exemplary embodiment of the cleaning device of the present invention.

FIG. 5 is a top plan view of yet another exemplary embodiment of the cleaning device 30 of the present invention. Cleaning device 30 includes a rod member 32 having a first end 34 and a second end 36 where second end 36 comprises a looped end. Cleaning device 30 also includes a swab member 38 having a first end 40 and a second end 42 where first end 40 is attached to the second looped end 36 of rod member 32 and second end 42 comprises a tail 44 which can be like the tail of a kite where the tail can be of any length. Swab member 38 may comprise one or more materials that may comprise one or more fibers that can be braided or twisted with the tail end 44 of the swab member 38 comprising the unbraided and/or untwisted ends of the material(s) and/or fiber(s) that comprise the swab member 38. In addition, the swab member 38 may comprise a foam material and/or a microfiber material. It should be understood by those skilled in the art that swab member 38 (and 18 in FIG. 1) along with tail 44 (and 24 in FIG. 1) may together be referred to as a kite like tail with reference to the rod member component of the cleaning device of the present invention.

In the exemplary embodiment shown in FIG. 5, the length of the looped end 36 of rod member 32 appears to be nearly equal to the length of the straight end 34 of rod member 32 when the length of looped end 36 is considered to be its length when secured in a looped configuration (i.e. its length is half of what it would be if the looped end 36 were opened up such that it was no longer in a looped configuration). In addition, swab member 38 is longer in length than looped end 36 of rod member 32 when the length of looped end 36 is considered to be its length when secured in a looped configuration (i.e. its length is half of what it would be if the looped end 36 were opened up such that it was no longer in a looped configuration). The lengths of the swab member 38, the second looped end 36 of rod member 32, and the first straight end 34 of rod member 32 in the exemplary embodiment of cleaning device 30 shown in FIG. 5 can also be seen in FIG. 6 which is a side elevational view of the exemplary embodiment of cleaning device 30 shown in FIG. 5. The polymer comprising rod member 32 may be an organic polymer thermoplastic which, in one exemplary embodiment, may be a polyether ether ketone. The rod member is preferably a thin, flexible, threadlike member.

Figure 6:
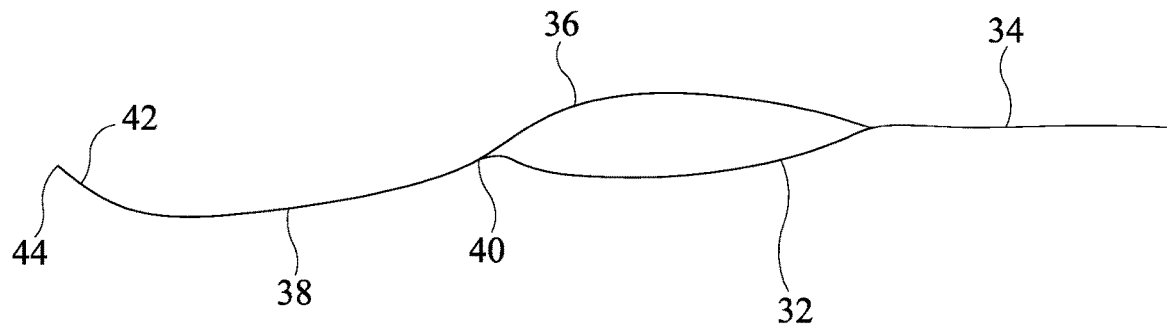
FIG. 6 is a side elevational view of the exemplary embodiment of the cleaning device of the present invention shown in FIG. 5.
Figure 7:
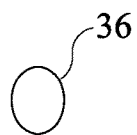
FIG. 7 is a magnified cross-sectional view of the exemplary embodiment of the cleaning device shown in FIG. 5 taken along line 7-7.
Figure 8:
FIG. 8 is a magnified cross-sectional view of the exemplary embodiment of the cleaning device shown in FIG. 5 taken along line 8-8.

FIG. 7 is a magnified cross-sectional view of the exemplary embodiment of the cleaning device shown in FIG. 5 taken along line 7-7 and FIG. 8 is a magnified cross-sectional view of the exemplary embodiment of the cleaning device shown in FIG. 5 taken along line 8-8. As shown in FIGS. 7 and 8, the diameter of looped end 36 of rod member 32 is smaller than the diameter of straight end 34 of rod member 32. Likewise, the outer circumference of looped end 36 of rod member 32 is smaller than the outer circumference of straight end 34 of rod member 32. Further as shown in FIGS. 7 and 8, straight end 34 of rod member 32 may comprise two thicknesses of second looped end 36 of rod member 32 where the two thicknesses that comprise the straight end 34 are fused or bonded together or co-extruded such that the straight and looped ends 34, 36 of rod member 32 are continuous with one another. As previously described above with reference to the exemplary embodiment shown in FIGS. 5 and 6, the looped end 36 of rod member 32 is approximately the same in length as straight end 34 of rod member 32. However, depending on the type of instrument that cleaning device 30 of the present invention is designed to clean, looped end 36 of rod member 32 may be longer or shorter in length than straight end 34 of rod member 32.

Further, with respect to FIGS. 5 and 6, swab member 38 may be attached to second looped end 36 of rod member 32 by having a portion of second looped end 36 of rod member 32 traverse through a portion of first end 40 of swab member 38 such that swab member 38 is capable of being rotated about and through second looped end 36 of rod member 32. In addition, such attachment would allow swab member 38 to slide along the length of second looped end 36 of rod member 32. In the exemplary embodiment shown in FIGS. 5 and 6, swab member 38 is longer in length than second looped end 36 of rod member 32 when the length of second looped end 36 is considered to be its length in the secured loop configuration shown. However, in still other embodiments, swab member 38 may be equal to, or shorter in length than, second looped member 36 of rod member 32.

The exemplary embodiment shown in FIG. 5 includes a swab member 38 that comprises materials and/or fibers that are twisted in relation to one another to form the swab member while the exemplary embodiment shown in FIG. 1 includes a swab member 18 that comprises materials and/or fibers that are braided in relation to one another to form the swab member. It should also be understood by those skilled in the art that the swab member may comprise one or more materials and/or one or more fibers that are secured to one another in other ways or by other means besides twisting or braiding such as but not limited to, for example, bonding with heat and/or pressure and/or bonding with chemicals or laminates. However, depending on the type of instrument that the cleaning device 10 of the present invention is designed to clean, it may not be beneficial to use any additional bonding or securing means other than twisting or braiding of the materials and/or fibers that comprise the swab member as it could result in the introduction of potential contaminants in addition to the ones that the cleaning device 10 is trying to remove. This may be particularly relevant with respect to cleaning medical instruments and/or other instruments that need to be sterilized before use.

The detailed description of exemplary embodiments of the invention herein shows various exemplary embodiments and the best modes, known to the inventor at this time, of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that ale known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The invention claimed is:

1. A cleaning device comprising:
   a swab member having a plurality of material members connected to one another to form the swab member; and
   a flexible rod member connected to the swab member wherein the flexible rod member includes a looped end that traverses through and is embedded into each of the plurality of material members that form the swab member.

2. The cleaning device of claim 1 wherein the flexible rod member comprises a polymer.

3. The cleaning device of claim 2 wherein the polymer comprises an organic polymer thermoplastic.

4. The cleaning device of claim 3 wherein the organic polymer thermoplastic comprises polyether ether ketone.

5. The cleaning device of claim 1 wherein the plurality of material members comprises at least one of a foam material member and a microfiber material member.

6. The cleaning device of claim 1 wherein the flexible rod member has a straight end that is opposite the looped end.

7. The cleaning device of claim 6 wherein the flexible rod member comprises a polymer.

8. The cleaning device of claim 6 wherein a portion of the flexible rod member that defines the looped end of the flexible rod member has a smaller diameter than a portion of the flexible rod member that defines the straight end of the flexible rod member.

9. The cleaning device of claim 6 wherein the looped end is longer in length than the straight end.

10. The cleaning device of claim 9 wherein the swab member is shorter in length than the looped end.

11. The cleaning device of claim 6 wherein the looped end is equal in length to the straight end or less in length than the straight end.

12. The cleaning device of claim 11 wherein the swab member is longer in length than the looped end.

13. The cleaning device of claim 1 wherein the swab member comprises a first end and a second end wherein the first end is connected to the looped end of the flexible rod member and the second end has a tail comprising unconnected ends of the plurality of material members.

14. The cleaning device of claim 13 wherein the plurality of material members connected to one another comprise a plurality of material members that are braided in relation to one another.

15. The cleaning device of claim 13 wherein the plurality of material members connected to one another comprise a plurality of material members that are twisted in relation to one another.

16. The cleaning device of claim 8 wherein the outer circumference of a portion of the flexible rod member that defines the straight end of the flexible rod member is larger than the outer circumference of a portion of the flexible rod member that defines the looped end of the flexible rod member.

17. The cleaning device of claim 8 wherein the straight end is double the thickness of a strand or filament forming the looped end wherein the strands or filaments forming the straight end are fused together or co-extruded.

* * * * *